US008277857B2

(12) United States Patent
Shimizu et al.

(10) Patent No.: US 8,277,857 B2
(45) Date of Patent: Oct. 2, 2012

(54) METHOD FOR PRODUCING FERMENTED MILK

(75) Inventors: Kanetada Shimizu, Zama (JP); Sumiko Yonezawa, Yamato (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 37 days.

(21) Appl. No.: 12/810,407

(22) PCT Filed: Apr. 17, 2009

(86) PCT No.: PCT/JP2009/057760
§ 371 (c)(1),
(2), (4) Date: Jun. 24, 2010

(87) PCT Pub. No.: WO2009/150897
PCT Pub. Date: Dec. 17, 2009

(65) Prior Publication Data
US 2010/0266725 A1    Oct. 21, 2010

(30) Foreign Application Priority Data
Jun. 11, 2008 (JP) .................................. 2008-152949

(51) Int. Cl.
*A23C 9/12* (2006.01)
(52) U.S. Cl. ............... 426/43; 426/34; 426/42; 426/580
(58) Field of Classification Search .............. 426/34, 426/42, 43, 580, 582, 583
See application file for complete search history.

(56) References Cited

U.S. PATENT DOCUMENTS 7,718,171 B2 *   5/2010   Flambard ...................... 424/115

FOREIGN PATENT DOCUMENTS

| AU | 2007333620 A1 | 8/2008 |
|---|---|---|
| EP | 0 974 268 A1 | 1/2000 |
| EP | 1989942 A1 | 11/2008 |
| EP | 2112219 A1 | 10/2009 |
| FR | 2842707 A1 | 1/2004 |
| JP | 63094938 A | 4/1988 |
| JP | 8187072 A | 7/1996 |
| JP | 9023848 A | 1/1997 |
| JP | 10-229819 | 9/1998 |
| JP | 3068484 | 9/1998 |
| JP | 2002-335860 | 11/2002 |
| JP | 3364491 | 11/2002 |
| JP | 2004-261003 A | 9/2004 |
| WO | 2008/038075 A2 | 4/2008 |
| WO | 2008/043856 A1 | 4/2008 |
| WO | 2008/148561 A1 | 12/2008 |
| WO | 2010023290 A2 | 3/2010 |

OTHER PUBLICATIONS

Japanese Patent Office; Search Report in International Patent Application No. PCT/JP2009/057760 dated May 19, 2009; 10 pages.
Pillidge et al.; "Exchanging Lactocepin Plasmids in Lactococcal Starters to Study Bitterness Development in Gouda Cheese: a preliminary investigation."; 2003 Elsevier Science Ltd.; 10 pages.
Broadbent et al.; "Conversion of *Lactococcus lactis* Cell Envelope Proteinase Specificity by Partial Allele Exchange."; 2006 The Society for Applied Microbiology; 12 pages.
Yonezawa et al.; "*Lactococcus lactis* Tono Kongo Hakko ni Yoru Bifidus-kin no Zoshoku Sokushin Narabi ni Seizonsei Kaizen Sayo Oyobi Sono Kijo Kaiseki"; 2008 Journal of Japan Society for Lactic Acid Bacteria; 2 pages.
Odamaki et al.; "3P0609A *Lactococcus lactis* ni Yoru Bifidus-kin no Hakko Nyuchu ni Okeru Horzonsei Kaizen Sayo"; 2009; 2 pages.
Korean Patent Office; Office Action in Korean Patent Application No. 10-2010-7014209 mailed on Dec. 1, 2010.
Dudley, E.G. et al., "*Lactococcus lactis* LM0230 contains a single aminotransferase involved in aspartate biosynthesis, which is essential for growth, in milk", Microbiology, 2001, Vo. 147, pp. 215-224.
Habimana, O., et al., "Positive role of cell wall anchored proteinase PrtP in adhesion of lactococci", BMC Microbiology, 2007, vol. 7(36), pp. 1-8.
Reid, J.R. et al., Applied and Environmental Microbiology, 1994, vol. 60, No. 3, pp. 801-806.
Chemical Abstracts Accession No. 2002:606860&RU2175192 C1 (Andreeva et al.) Oct. 27, 2001.
Chemical Abstracts Accession No. 2005:1036413&RU2260978 C2 (Besserezhnov) Sep. 27, 2005.
Journal of Applied Microbiology, 2006, vol. 100, pp. 1307-1317.
European Search Report issued in PCT Application No. PCT/JP2009/057760, 9 pages, dated Mar. 2, 2011.
Comes, Ana M. P. et al., Growth Enhancement of Bifidobacterium lactis Bo and *Lactobacillus acidophilus* Ki by Milk Hydrolyzates, Journal of Dairy Science, 1998, pp. 2817-2825, vol. 81 No. 11.
Yonezawa, S. et al., Improved growth of bifidobacteria by cocultivation with *Lactococcus lactis* subspecies *lactis*, Journal of Dairy Science, 2010, pp. 1815-1823, vol. 93, No. 5.
Liu, Mengjin et al., The proteolytic system of lactic acid bacteria revisited: a genomic comparison, BMC Genomics, 2010, 15 pages, vol. 11, No. 36.
Klaver et al., Growth and survival of bifidobacteria in milk, Netherlands Milk and Dariy Journal, Jan. 1, 1993, pp. 151-164, vol. 47, No. 3/4.
Kheadr, E.S., Viability of Bifidobacterium longum Grown Alone or in Association with Some Strains of Lactic Acid Bacteria Under Refrigeration, Alexandria Journal for Food Science and Technology, 2007, pp. 45-62, vol. 4, No. 1.
Abe F. et al., Effect of production conditions on the stability of a human bifidobacterial species Bifidobacterium longum in yogurt, Letters in Applied Microbiology, Dec. 2009, pp. 715-720, vol. 49, No. 6.
Office Action issued in European Patent Application No. 09762328.4, mailed Dec. 27, 2011, 7 pages.

* cited by examiner

*Primary Examiner* — Leslie Wong
(74) *Attorney, Agent, or Firm* — Wood, Herron & Evans, LLP

(57) ABSTRACT

The present invention provides a method for producing fermented milk, the method employing a lactic acid bacterium capable of improving proliferative properties of *Bifidobacterium*, and a fermented milk prepared by the production method. Specifically, the present invention provides a method for producing a fermented milk, including fermenting a fermentation base using both *Lactococcus lactis* strain having cell wall-enveloped proteinase, PrtP, and bacteria belonging to a genus *Bifidobacterium*, and a fermented milk prepared by the production method.

2 Claims, 1 Drawing Sheet

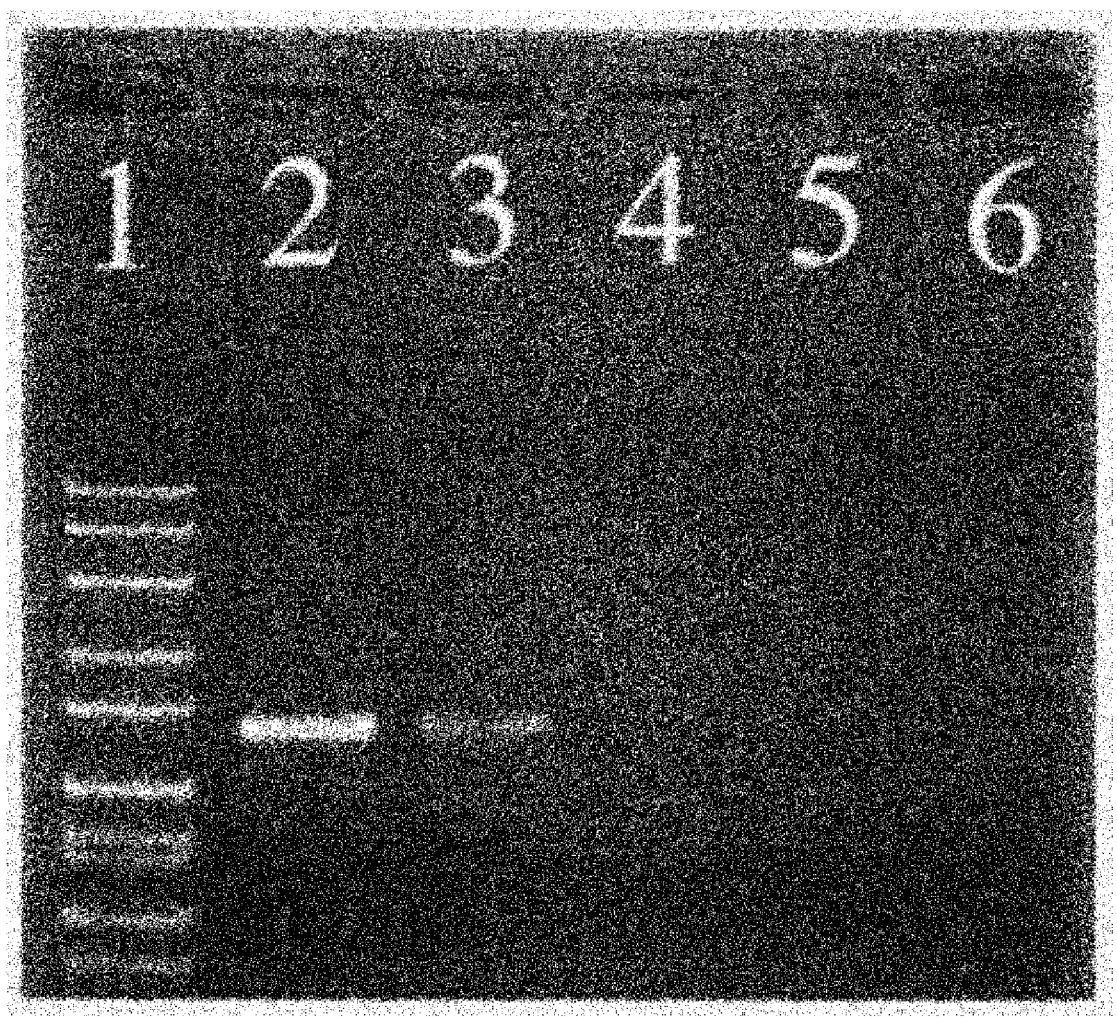

METHOD FOR PRODUCING FERMENTED MILK

This application is a 371 of PCT/JP2009/057760 filed Apr. 17, 2009.

TECHNICAL FIELD

The present invention relates to a method for producing fermented milk obtained by co-fermentation of *Lactococcus lactis* strain having cell wall-enveloped proteinase, PrtP, and bacteria belonging to a genus *Bifidobacterium*.

Priority is claimed on Japanese Patent Application No. 2008-152949, filed on Jun. 11, 2008, the contents of which are incorporated herein by reference.

BACKGROUND OF THE INVENTION

Bacteria belonging to the genus *Bifidobacterium*, which are herein referred to as *Bifidobacterium*, is one of predominant bacterial strains in intestinal microflora formed in the human intestinal tract. It is known that *Bifidobacterium* have an intestinal function-regulating activity, an immuno-stimulating activity, and an anti-cancer activity.

Accordingly, demands for food products containing viable *Bifidobacterium* such as milk fermented with *Bifidobacterium* or the like are increasing in accordance with an increase of health consciousness of consumers.

*Bifidobacterium* exhibits a poor proliferation potency in a milk medium. Accordingly, various growth-stimulating substances, such as yeast extract and the like, are generally formulated in fermented milk so that the *Bifidobacterium* is contained therein at a constant content, for example, $1 \times 10^7$ CFU/ml. However, the growth-stimulating substances are generally expensive and may degrade the taste.

Various methods for promoting the growth of *Bifidobacterium* or improving the survivability thereof during storage by fermentation with *Bifidobacterium* and another lactic acid bacterium without adding any growth-stimulating substances or the like have been disclosed. For example, (1) yoghurt containing *Lactococcus lactis* subsp. *lactis*, *Lactococcus lactis* subsp. *cremoris*, and *Bifidobacterium*, and a method for preparing the yoghurt have been disclosed (see, for example, Patent Document 1), with respect to a method for promoting the growth of *Bifidobacterium* to prepare fermented milk.

For example, (2) a method for fermenting milk with *Bifidobacterium*, including cultivating *Bifidobacterium* breve together with *Lactococcus lactis* subsp. *lactis*, which forms neither diacetyl nor acetoin, in a medium containing milk as the main component thereof has been disclosed (see, for example, Patent Document 2), with respect to a method for improving the survivability of *Bifidobacterium* during storage of fermented milk.

[Patent Document 1] Japanese Patent Publication No. 3,364,491
[Patent Document 2] Japanese Patent Publication No. 3,068,484

DISCLOSURE OF THE INVENTION

Problems to be Solved by the Invention

However, it cannot always be said that the method described above in (1) has sufficient effects of promoting the growth of *Bifidobacterium* and reducing the period of fermentation. In addition, while it is reported that the growth of *Bifidobacterium* is promoted under conditions where the two strains, *Lactococcus lactis* subsp. *lactis* and *Lactococcus lactis* subsp. *cremoris*, are present, there is no mention of the effects in the case where *Lactococcus lactis* subsp. *lactis* or *Lactococcus lactis* subsp. *cremoris* is each employed solely.

In the method described above in (2), on the other hand, the effects of both promoting proliferation and improving survival properties are observed by employing a mixture of the given strain of *Bifidobacterium* and the particular strain of lactic acid bacterium, but there is no mention of *Bifidobacterium* other than *Bifidobacterium* breve, for example, *Bifidobacterium longum*, which is used widely in foods.

The present invention has for an object thereof the provision of a method for producing fermented milk using lactic acid bacteria which improve the proliferative properties of *Bifidobacterium*, and fermented milk prepared in accordance with the production method.

Means to Solve the Problems

The inventors of the present invention intensively investigated so as to solve the above-mentioned problems, and as a result, the inventors found that the proliferation of *Bifidobacterium* can be promoted when a *Lactococcus lactis* strain possessing cell wall-enveloped proteinase, PrtP, is fermented in a mixture with a strain of *Bifidobacterium*, and thus the inventors completed the present invention.

That is, the present invention provides a method for producing fermented milk, including: fermenting a fermentation base using both *Lactococcus lactis* strain having cell wall-enveloped proteinase, PrtP, and bacteria belonging to a genus *Bifidobacterium*.

The present invention also provides the above-mentioned method for producing a fermented milk, wherein the bacteria belonging to the genus *Bifidobacterium* is *Bifidobacterium longum*.

The present invention also provides the above-mentioned method for producing a fermented milk, wherein the *Bifidobacterium longum* is *Bifidobacterium longum* ATCC BAA-999 and/or *Bifidobacterium longum* type strain ATCC 15700.

In addition, the present invention provides a fermented milk prepared by any of the above-mentioned methods for producing a fermented milk.

EFFECTS OF THE INVENTION

In accordance with the method for producing fermented milk according to the present invention, fermented milk containing a great amount of *Bifidobacterium*, particularly *Bifidobacterium longum* can be efficiently produced as never before. In addition, the fermented milk produced by the method of the present invention for producing fermented milk exhibits further high intestinal function-regulating effects and is useful for health control.

BRIEF DESCRIPTION OF THE DRAWING

FIG. 1 shows the band pattern of PCR products which were obtained by PCR employing DNA from respective strains of *Lactococcus lactis* as the template and primers for detecting a gene for a PrtP enzyme, and separated by electrophoresis and detected by staining.

DETAILED DESCRIPTION OF THE INVENTION

Lactic acid bacteria which can be employed in the present invention are of *Lactococcus lactis* strain possessing a PrtP enzyme. PrtP enzyme is an enzyme which is located in the cell membrane and has an active site exposed on the cell surface. Several lactic acid bacteria strains possessing a PrtP enzyme have been reported which possess PrtP, for example, in strains of the genus *Lactococcus*, such as *Lactococcus lactis* subsp. *cremoris*, *Lactococcus lactis* subsp. *lactis*, and others.

Up until now, PrtP enzymes derived from *Lactococcus lactis* have been known to be of the type $P_I$ (which does not degrade alpha-casein well, but degrades beta-casein well from the proximity of the C-terminal), the type $P_{III}$ (which degrades alpha- and beta-caseins well from both the C-terminal and the N-terminal), and intermediate types ($P_I/P_{III}$) between these (see, for example, Reid, J. R. et al., Applied and Environmental Microbiology, 1994, vol. 60, No. 3, pp. 801-806).

In particular, PrtP enzymes derived from *Lactococcus lactis* include, for example, PrtP enzymes, the gene sequences of which have been deposited as Accession Nos. AY542690 and AY542691, and others at the NCBI (National Center for Biotechnology Information).

Whether or not a given lactic acid bacterium is one which has a PrtP enzyme can be identified, for example, by employing gene analysis techniques, such as PCR (Polymerase Chain Reaction) and others, to examine whether or not the bacterium carries a gene coding a PrtP enzyme.

PrtP enzymes, which have their enzymatically active site on the outside of the cell, are capable of degrading proteins in media. For example, when a lactic acid bacterium possessing a PrtP enzyme proliferates in a milk medium, the PrtP enzyme degrades milk proteins in the milk medium, providing oligopeptides and amino acids required for the growth of lactic acid bacteria. As a result, strains of *Lactococcus lactis* having a PrtP enzyme are characterized in that they rapidly proliferate and are highly fermentative, so that when cultured in the range of temperatures of 25 to 30° C. for 16 hours in a 10% (W/W) reconstituted nonfat-milk-powder medium, they can cause the medium to become coagulated. The characteristics of having this proliferative property and of being highly fermentative can also be used to detect strains of *Lactococcus lactis* having a PrtP enzyme. In addition, it is also possible to detect strains of *Lactococcus lactis* having a PrtP enzyme by detecting the PrtP enzyme activity.

Strains of *Lactococcus lactis* which can be employed in the present invention are not limited specifically, if they have a PrtP enzyme. Preferable strains are *Lactococcus lactis* subsp. *cremoris*, *Lactococcus lactis* subsp. *lactis*, and the like, because they have been used in the past as raw materials of milk products, such as fermented milk and the like, which use *Bifidobacterium* as a raw material, and thus are believed to have high levels of safety. *Lactococcus lactis* having a PrtP enzyme include, for example, *Lactococcus lactis* subsp. *cremoris* NBRC $100676^T$, *Lactococcus lactis* subsp. *lactis* JCM 20101, and others.

The following provides an explanation in more detail of *Lactococcus lactis* having a PrtP enzyme which can be employed in the present invention, and the effects of promoting the proliferation of *Bifidobacterium*.

1. Detection of Whether Strains of *Lactococcus lactis* have a PrtP Enzyme

Examinations were made to determine whether or not the following strains have a PrtP enzyme: *Lactococcus lactis* subsp. *cremoris* NBRC $100676^T$ (ATCC $19257^T$), *Lactococcus lactis* subsp. *cremoris* ATCC-9625, *Lactococcus lactis* subsp. *lactis* NBRC 12007 (NCDO 497), *Lactococcus lactis* subsp. *lactis* JCM 20101, and *Lactococcus lactis* subsp. *lactis* JCM 20128.

Specifically, each of these strains was inoculated to a level of 3% into a Difco® M17 Broth (Becton, Dickinson and Company) supplemented with lactose and glucose at 0.5% each, and cultured at 30° C. for 16 hours. Cells were obtained by centrifugation and DNA was extracted employing the DNeasy Blood and Tissue kit (QIAGEN) to examine, by a PCR method, whether or not the strain has a PrtP enzyme. PCR was performed according to the procedures described in a reference (Journal of Applied Microbiology, 2006, vol. 100, pp. 1307-1317). The primers used were a primer set of a forward primer GBf (GCAAATACGGTGACGGCTGCGA) and a reverse primer GB2r (TGAGCATTATAATAGGTCT-TCTTCC), or a forward primer GHf (CAAATACGGT-GACGGCTGCTAA) and a reverse primer GH2r (TAGCAT-TATAATAGGTCTTCGTCA).

FIG. 1 shows the band pattern in which PCR products were separated by electrophoresis and detected by staining. In FIG. 1, "1" represents a lane where molecular weight markers were run; "2" represents a lane where the PCR product from *Lactococcus lactis* subsp. *cremoris* NBRC $100676^T$ was run; "3" represents a lane where the PCR product from *Lactococcus lactis* subsp. *lactis* JCM 20101 was run; "4" represents a lane where the PCR product from *Lactococcus lactis* subsp. *lactis* NBRC 12007 was run; "5" represents a lane where the PCR product from *Lactococcus lactis* subsp. *lactis* JCM 20128 was run; and "6" represents a lane where the PCR product from *Lactococcus lactis* subsp. *cremoris* ATCC-9625 was run. From these results, it was ascertained that *Lactococcus lactis* subsp. *cremoris* NBRC $100676^T$ and *Lactococcus lactis* subsp. *lactis* JCM 20101 carry a gene for PrtP. On the other hand, it turned out that a gene for PrtP is not carried by each of *Lactococcus lactis* subsp. *cremoris* ATCC-9625, *Lactococcus lactis* subsp. *lactis* NBRC 12007, and *Lactococcus lactis* subsp. *lactis* JCM 20128.

2. Test with Respect to Fermentability of *Lactococcus lactis* on Milk Medium

First, each of the strains was inoculated to a level of 3% into a Difco® M17 Broth (Becton, Dickinson and Company) supplemented with lactose and glucose at 0.5% each, and cultured at 30° C. for 16 hours. Cells were harvested by centrifugation, washed, and then suspended at the same volume as that of the first culture medium in a milk medium having the composition described below, thereby making a seed culture.

Second, a milk medium containing 1% (W/W) of glucose and 10% (W/W) of a reconstituted nonfat milk powder was sterilized at 95° C. for 30 minutes. Then, the seed culture of each of the above-described strains was inoculated to a level of 3% and cultured at 30° C. for 16 hours. After the obtained culture medium was rapidly cooled, the curdled state was observed, and the pH and the viable count of the contained lactic acid bacteria were measured. The viable count was measured using commercially available BCP added plate count agar (Eikenkizai Co., Ltd.) flat plates.

The measurement results are shown in Table 1. *Lactococcus lactis* subsp. *cremoris* NBRC $100676^T$ and *Lactococcus lactis* subsp. *lactis* JCM 20101 which have a gene for a PrtP enzyme resulted in the decrease of pH to 5.0 or lower and the coagulation of the medium. In addition, the viable count of lactic acid bacteria contained was $3 \times 10^8$ CFU/g or higher, and it turned out that these strains had very good properties in terms of proliferation and fermentation. In contrast, each of *Lactococcus lactis* subsp. *cremoris* ATCC-9625, *Lactococcus lactis* subsp. *lactis* NBRC 12007, and *Lactococcus lactis* subsp. *lactis* JCM 20128 which are devoid of a gene for a PrtP enzyme resulted in a pH of 5.5 or higher, no coagulation of the medium, and the viable count of lactic acid bacteria of $1 \times 10^8$ CFU/g or lower.

TABLE 1

| | | Culture condition (30° C., 16 hours) | | |
|---|---|---|---|---|
| Strain | PrtP | Number of bacteria (CFU/g) | pH | State of coagulation |
| NBRC 100676$^T$ | + | $3.5 \times 10^8$ | 4.9 | Coagulation |
| JCM 20101 | + | $1.3 \times 10^9$ | 4.8 | Coagulation |
| NBRC 12007 | − | $3.0 \times 10^7$ | 6.0 | No coagulation |
| JCM 20128 | − | $4.4 \times 10^7$ | 5.8 | No coagulation |
| ATCC-9625 | − | $4.2 \times 10^7$ | 5.6 | No coagulation |

3. Co-cultivation Test with *Bifidobacterium*

First, *Bifidobacterium longum* ATCC BAA-999 was prepared in the method described in Example 1 described below.

In addition, each of the *Lactococcus lactis* strains was inoculated to a level of 3% into a Difco® M17 Broth (Becton, Dickinson and Company) supplemented with lactose and glucose at 0.5% each, and cultured at 30° C. for 16 hours. Cells were harvested by centrifugation, washed, and then suspended at the same volume as that of the first culture medium in a milk medium having the composition described below, thereby making a seed culture.

A milk medium containing 1% (W/W) of glucose and 10% (W/W) of a reconstituted nonfat milk powder was sterilized at 90° C. for 10 minutes. Then, 1% of the seed culture of each of the *Lactococcus lactis* strains prepared as described above and 1% of the culture of *Bifidobacterium longum* ATCC BAA-999 were inoculated into the milk medium, and cultivated at 37° C. for 16 hours to obtain fermented milk. The resulting fermented milk was rapidly cooled, and the pH thereof and the viable count of the contained *Bifidobacterium* were measured. The measurement results are shown in Table 2. The viable count of the *Bifidobacterium* was measured using TOS propionate agar (manufactured by Yakult Pharmaceutical Industry Co., Ltd.) flat plates.

The measurement results are shown in Table 2. When culturing was carried out in the mixture with each of *Lactococcus lactis* subsp. *cremoris* NBRC 100676$^T$ and *Lactococcus lactis* subsp. *lactis* JCM 20101 which have a gene for a PrtP enzyme, the pH was decreased down to 5.0 or lower, a coagulated fermented milk was produced, and viable count of *Bifidobacterium* reached $2 \times 10^8$ CFU/g or higher. In contrast, when culturing was carried out in the mixture with each of *Lactococcus lactis* subsp. *cremoris* ATCC-9625, *Lactococcus lactis* subsp. *lactis* NBRC 12007, and *Lactococcus lactis* subsp. *lactis* JCM 20128 which are devoid of a gene for a PrtP enzyme, the pH was 5.5 or higher, no coagulation of the fermentation base occurred, and viable count of *Bifidobacterium* was $2 \times 10^7$ CFU/g or lower.

Therefore, it is clear that strains of *Lactococcus lactis* which have a gene for a PrtP enzyme are superior in promoting proliferation of *Bifidobacterium*, as compared to those devoid of a gene for a PrtP enzyme, and that culturing of a *Lactococcus lactis* strain which has a gene for a PrtP enzyme in a mixture with *Bifidobacterium* can produce an effect of promoting the proliferation of *Bifidobacterium*.

TABLE 2

| | | ATCC BAA-999 | |
|---|---|---|---|
| Strain | PrtP | Number of bacteria (CFU/g) | pH |
| NBRC 100676$^T$ | + | $2.8 \times 10^8$ | 4.6 |
| JCM 20101 | + | $2.4 \times 10^8$ | 4.93 |
| NBRC 12007 | − | $7.0 \times 10^6$ | 5.59 |
| JCM 20128 | − | $1.7 \times 10^7$ | 5.57 |
| ATCC-9625 | − | $1.5 \times 10^7$ | 5.59 |

4. Comparison of the Lactic Acid Bacteria as Described in Patent Documents 1 and 2 to the *Lactococcus lactis* Strains of the Present Invention First, seed cultures of *Lactococcus lactis* subsp. *cremoris* NBRC 100676$^T$ and *Lactococcus lactis* subsp. *lactis* JCM 20101 which have a gene for a PrtP enzyme were prepared in the method described in Section 3 above.

Second, a culture of *Bifidobacterium longum* ATCC BAA-999 was prepared in the method described in Example 1 described below.

In addition, 1,000 mL of a 10% (W/W) reconstituted nonfat milk powder medium supplemented with 0.2% (W/W) of yeast extract (Difco) was sterilized at 90° C. for 30 minutes. Then, 30 mL of a culture of *Lactococcus lactis* subsp. *lactis* type strain ATCC 19435 as described in Patent Document 2 was inoculated into the reconstituted nonfat milk powder medium, and cultivated at 30° C. for 16 hours to prepare a culture of *Lactococcus lactis* subsp. *lactis* type strain ATCC 19435.

Separately, a 10% (W/W) reconstituted nonfat milk powder medium was sterilized at 90° C. for 10 minutes. Then, 1% of the culture of *Lactococcus lactis* subsp. *cremoris* NBRC 100676$^T$, *Lactococcus lactis* subsp. *lactis* JCM 20101, or *Lactococcus lactis* subsp. *lactis* type strain ATCC 19435 prepared as described above and 1% of the culture of *Bifidobacterium longum* ATCC BAA-999 were inoculated into the reconstituted nonfat milk powder medium, and cultivated at 37° C. for 16 hours to produce fermented milk. The resulting fermented milk was rapidly cooled, and the pH thereof and viable count of the contained *Bifidobacterium* were measured.

On the other hand, 10% (W/W) reconstituted nonfat milk powder medium was sterilized at 90° C. for 10 minutes. Then, 1% of the culture of *Bifidobacterium longum* ATCC BAA-999 prepared as described above and 2% of the mixture "EZAL MA14" (manufactured by Rhodia) of *Lactococcus lactis* subsp. *lactis* and *Lactococcus lactis* subsp. *cremoris* as described in the Patent Document 1 were inoculated into the reconstituted nonfat milk powder medium, and cultivated at 37° C. until the medium reached a pH of 4.6 to obtain fermented milk. The viable count of *Bifidobacterium* in the fermented milk thus produced was measured in a similar way. The "EZAL MA14" is a mixture which corresponds to the "EZAL MR014" (manufactured by Rhodia) described in Patent Document 1.

The results are shown in Table 3. In the case of *Lactococcus lactis* subsp. *cremoris* NBRC 100676$^T$ and *Lactococcus lactis* subsp. *lactis* JCM 20101 which has a gene for a PrtP enzyme, the viable count of *Bifidobacterium* reached around $3 \times 10^8$ CFU/g. In contrast, the fermented milk produced employing the "EZAL MA14" resulted in the decrease of pH to 5.0 or lower and the coagulation of the fermentation base, while no *Bifidobacterium* was detected from solutions diluted $10^6$ times of the fermented milk, indicating that the viable count of *Bifidobacterium* contained in the fermented milk was $1 \times 10^6$ CFU/g or less.

Therefore, it is clear that the effects of promoting the growth of *Bifidobacterium* and reducing the period of fermentation cannot be achieved to a sufficient degree when *Lactococcus lactis* subsp. *lactis* and *Lactococcus lactis* subsp. *cremoris* as described in Patent Document 1 are subjected to culturing in a mixture with *Bifidobacterium longum*.

In the case of the fermented milk produced employing *Lactococcus lactis* subsp. *lactis* type strain ATCC 19435 as described in Patent Document 2, the pH was 5.0 or higher and no coagulation occurred, and fermented milk was not produced, when the fermentation was performed for 16 hours.

The viable count of *Bifidobacterium* at the end of the fermentation was $1 \times 10^8$ CFU/g or less, which indicates that the effect of promoting the proliferation of *Bifidobacterium* was remarkably weak, as compared to strains of *Lactococcus lactis* which have a gene for a PrtP enzyme according to the present invention.

These results revealed that *Lactococcus lactis* subsp. *cremoris* NBRC 100676$^T$ and *Lactococcus lactis* subsp. *lactis* JCM 20101, which are of *Lactococcus lactis* having a gene for a PrtP enzyme, have a superior effect of promoting proliferation on bacteria of the genus *Bifidobacterium*.

TABLE 3

| | | ATCC BAA-999 | |
|---|---|---|---|
| Strain | PrtP | Number of bacteria (CFU/g) | pH |
| NBRC 100676$^T$ | + | $3.0 \times 10^8$ | 4.6 |
| JCM 20101 | + | $3.3 \times 10^8$ | 4.8 |
| Prior art (EZAL MA14) | − | Not detected | 4.6 |
| Prior art (ATCC 19435) | − | $9.2 \times 10^7$ | 5.4 |

In the present invention, although it is unclear why the effect of promoting the growth of *Bifidobacterium* is achieved by a mixed culture of a strain of *Lactococcus lactis* which has a PrtP enzyme and *Bifidobacterium*, it is presumed that the reason is that milk proteins in a milk medium are hydrolyzed by PrtP which *Lactococcus lactis* has, resulting in oligopeptides having an effect of promoting the proliferation of *Bifidobacterium*.

Strains of *Bifidobacterium* which can be employed in the present invention are not limited specifically. Preferable strains are *Bifidobacterium longum*, because the effect of promoting proliferation by *Lactococcus lactis* having a PrtP enzyme is achieved to a more remarkable degree. In particular, *Bifidobacterium longum* ATCC BAA-999 and *Bifidobacterium longum* type strain ATCC 15700 are preferable.

In the present invention, although a preculture medium used for cultivating *Lactococcus lactis* having a PrtP enzyme and *Bifidobacterium* is not particularly limited provided that the preculture medium is usually used, the preculture medium is preferably a milk medium. The preculture medium is more preferably a reconstituted nonfat milk powder medium, since the reconstituted skim milk medium can be easily handled. It is preferable that the concentration of the reconstituted skim milk medium be 3% (W/W) or more, and more preferably 8% (W/W) or more. In addition, the preculture medium may contain growth-stimulating substances such as yeast extract or reducing agents such as L-cysteine. It is particularly preferable that a growth-stimulating substance be formulated in the preculture medium, since *Bifidobacterium* exhibits a low level of proliferation in the milk medium. Specifically, a culture medium containing 0.1 to 1% (W/W) of yeast extract may be used. The preculture medium is subjected to sterilization for the use. The sterilization may be performed in accordance with a conventional method, specifically performed by heating at 80 to 122° C. for 5 to 40 minutes, preferably at 85 to 95° C. for 5 to 35 minutes.

In the present invention, the fermentation base medium to be used for fermentation with *Bifidobacterium* and *Lactococcus lactis* having a PrtP enzyme is not particularly limited, provided that the fermentation base medium is usually used to produce fermented milk. The fermentation base medium may be prepared, for example, by formulating a sweetener such as sucrose, pectin, fruit, fruit juice, agar, gelatin, oil and fat, flavor, coloring agent, stabilizer, reducing agent, or the like, in cow's milk, skim milk, fresh cream, butter, whole milk powder, powdered skim milk, or the like, as needed, followed by sterilizing, homogenizing, cooling, and the like, in accordance with conventional methods.

Although the inoculation ratio of *Bifidobacterium* and *Lactococcus lactis*, to be inoculated into the fermentation base medium as startars, is not particularly limited, the inoculation ratio is preferably 100:1 to 1:10, and more preferably 10:1 to 1:1. Although both amounts of *Bifidobacterium* and the bacteria belonging to the genus *Lactococcus* to be inoculated in the fermentation base medium are not particularly limited, it is preferable that the sum amount thereof be 0.01 to 10% (VAT), more preferably 0.1 to 5% (V/V), with respect to the amount of the fermentation base medium.

The lactic acid bacteria to be used in the present invention may further contain other lactic acid bacteria in addition to *Bifidobacterium* and *Lactococcus lactis*, unless the effects of *Lactococcus lactis* on the growth-stimulation of *Bifidobacterium* or the survivability-improvement thereof during storage are disturbed. Although the other lactic acid bacteria are not particularly limited, provided that the other lactic acid bacteria are usually used to produce fermented milk, the other lactic acid bacteria are preferably *Streptococcus thermophilus* and *Lactobacillus bulgaricus*. The inoculation ratio of the total content of *Bifidobacterium* and *Lactococcus lactis* to the total content of the other lactic acid bacteria, to be inoculated as starters into a fermentation base medium, is not particularly limited, unless the effects of the bacteria belonging to the genus *Lactococcus* on *Bifidobacterium* are disturbed, it is preferable that the inoculation ratio be within a range of 1,000:1 to 10:1.

It is preferable that co-cultivation temperature in the method for producing fermented milk according to the present invention be within a range of 30° C. to 40° C., more preferably 36° C. to 38° C. Both *Bifidobacterium* and *Lactococcus lactis* to be used in the present invention can be sufficiently proliferate in the above-mentioned temperature range. Although the cultivation time period is suitably determined depending on the kind of fermented milk to be prepared, the cultivation time period is preferably within a range of 5 to 18 hours.

The fermented milk obtained by cultivation may be provided as a food product, or may be homogeneously processed into a liquid state. In addition, fruit juice, fruit, or the like, may be suitably formulated in the fermented milk. The fermented milk may be put into a container by a conventionally-used method without any particular limitations.

EXAMPLES

In the following, the present invention will be circumstantially explained by indicating some examples. However, the present invention is not limited to the following examples.

Example 1

1,000 mL of a 10% (W/W) reconstituted nonfat milk powder medium was sterilized at 90° C. for 30 minutes. Then, 30 mL of a seed culture of *Lactococcus lactis* subsp. *cremoris* NBRC 100676$^T$ was inoculated into the reconstituted nonfat milk powder medium, and cultivated at 25° C. for 16 hours. In addition, 1,000 ml of an 11% (W/W) nonfat milk powder medium supplemented with 0.2% (W/W) of yeast extract was sterilized at 90° C. for 30 minutes. Then, 100 mL of a seed culture of *Bifidobacterium longum* ATCC BAA-999 was inoculated into the nonfat milk powder medium, and cultivated at 37° C. for 6 hours.

Apart from the above, 50 L of a base medium prepared by mixing and dissolving raw materials composed of skim milk powders, whole milk powders and sucrose, the base medium containing 0.5% (W/W) of butterfat, 8.0% (W/W) of nonfat milk solid component, 8.0% (W/W) of sucrose, and 0.2% (W/W) of pectin, was sterilized at 90° C. for 10 minutes, followed by cooling at 40° C. 50 mL of the above-obtained culture of the *Lactococcus lactis* subsp. *cremoris* NBRC $100676^T$ precultured and 500 mL of the above-obtained culture of *Bifidobacterium longum* ATCC BAA-999 precultured were inoculated into the sterilized base medium, followed by cultivating at 37° C. for 16 hours to obtain fermented milk. The fermented milk was immediately cooled while stirring, and the cooled fermented milk was homogenized at a pressure of 15 MPa, followed by putting the resultant into a glass container having a 200 mL capacity and then sealing the container to obtain a yoghurt drink. The obtained yoghurt drink had a lactic acid content of 0.7%, a pH of 4.6, and contained $5.0 \times 10^8$ CFU/g of *Bifidobacterium*. When the yoghurt drink was stored at 10° C. for 14 days, the viable count of *Bifidobacterium* was $2.5 \times 10^8$ CFU/g, and the survival rate thereof was 50%.

Example 2

1000 mL of a 10% (W/W) reconstituted skim milk medium supplemented with 1% of glucose was sterilized at 90° C. for 30 minutes. Then, 30 mL of a seed culture of *Lactococcus lactis* subsp. *lactis* JCM 20101 was inoculated into the reconstituted skim milk medium, and cultivated at 25° C. for 16 hours. On the other hand, 1000 mL of an 11% (W/W) skim milk medium containing 0.2% (W/W) yeast extract was sterilized at 90° C. for 30 minutes, and 100 ml of a seed culture of *Bifidobacterium breve* ATCC 15700 was inoculated thereinto, followed by cultivating at 37° C. for 16 hours. Apart form the above, 50 mL of a mixed culture of *Streptococcus thermophilus* (manufactured by HANSEN) and *Lactobacillus bulgaricus* (manufactured by HANSEN) was inoculated into 1500 ml of a 10% (W/W) reconstituted skim milk medium sterilized at 90° C. for 30 minutes, and then cultivated at 37° C. for 5 hours.

Apart from the above, 50 L of raw milk containing 3.0% (W/W) of butterfat and 9.0% (W/W) of nonfat milk solid component were heated at 70° C., homogenized at a pressure of 15 MPa, sterilized at 90° C. for 10 minutes, and then cooled at 40° C. Into the thus sterilized base medium, 500 mL of the culture of *Lactococcus lactis* subsp. *lactis* JCM 20101 precultured as described above, 500 mL of the culture of *Bifidobacterium breve* ATCC 15700, and 5 ml of the mixed culture of *Streptococcus thermophilus* and *Lactobacillus bulgaricus* were inoculated. The resultant was put into a resin container having a 500 mL capacity, and then the container was sealed. The bacteria were cultivated at 37° C. for 6 hours, and then immediately cooled. The thus obtained fermented milk had a lactic acid content of 0.7%, and a pH of 4.6, and contained $4.8 \times 10^8$ CFU/g of *Bifidobacterium*. When the fermented milk was stored at 10° C. for 14 days, the viable count of *Bifidobacterium* was $2.5 \times 10^8$ CFU/g, and the survival rate thereof was 38%.

INDUSTRIAL APPLICABILITY

Since fermented milk containing a greater count of viable *Bifidobacterium*, than ever before can be produced in accordance with the production method according to the present invention, the production method is available in the field of production of fermented milk or the like.

What is claimed is:
1. A method of producing a fermented milk, comprising: fermenting a fermentation base using both *Lactococcus lactis* strain having cell wall-enveloped proteinase, PrtP, and bacteria belonging to a genus *Bifidobacterium*, wherein the bacteria belonging to the genus *Bifidobacterium* is one or more selected from the group consisting of *Bifidobacterium longum* ATCC BAA-999 and *Bifidobacterium breve* type strain ATCC 15700.
2. A fermented milk prepared by the method of producing fermented milk according to claim 1.

* * * * *